(12) United States Patent
Tao et al.

(10) Patent No.: US 11,497,361 B2
(45) Date of Patent: Nov. 15, 2022

(54) ADJUSTABLE GAS DETECTION DEVICE FOR COAL BED

(71) Applicant: China University of Geosciences (Beijing), Beijing (CN)

(72) Inventors: Shu Tao, Beijing (CN); Dazhen Tang, Beijing (CN); Hao Xu, Beijing (CN); Song Li, Beijing (CN); Xinyang Men, Beijing (CN); Yaning Wu, Beijing (CN)

(*) Notice: Subject to any disclaimer, the term of this patent is extended or adjusted under 35 U.S.C. 154(b) by 435 days.

(21) Appl. No.: 16/679,217

(22) Filed: Nov. 10, 2019

(65) Prior Publication Data
US 2020/0315413 A1   Oct. 8, 2020

(30) Foreign Application Priority Data

Apr. 2, 2019  (CN) .......................... 201910264476.9

(51) Int. Cl.
*A47L 5/34* (2006.01)
*G01N 33/00* (2006.01)
*G01N 27/16* (2006.01)

(52) U.S. Cl.
CPC ............ *A47L 5/34* (2013.01); *G01N 33/0009* (2013.01); *G01N 27/16* (2013.01)

(58) Field of Classification Search
CPC .................................................. G01N 33/0009
See application file for complete search history.

(56) References Cited

U.S. PATENT DOCUMENTS

| | | | | |
|---|---|---|---|---|
| 7,051,577 B2* | 5/2006 | Komninos | ............. | G01M 3/24 73/40.7 |
| 7,420,664 B2* | 9/2008 | Treado | ................. | G01J 3/0227 901/47 |
| 7,588,726 B1* | 9/2009 | Mouradian | ........ | G01N 33/0009 702/22 |
| 9,772,271 B2* | 9/2017 | Peacock | ................. | G01N 15/06 |
| 2016/0177540 A1* | 6/2016 | Penza | ....................... | E02F 3/96 296/24.32 |
| 2018/0328808 A1* | 11/2018 | Jourdan | .................. | G01M 3/20 |

OTHER PUBLICATIONS

IRB 6650S Industrial Robot. ABB Data Sheet, https://search.abb.com/library/Download.aspx?DocumentID=PR10262EN_R6&LanguageCode=en&DocumentPartId=&Action=Launch (Year: 2021).*

* cited by examiner

*Primary Examiner* — Paul M. West
*Assistant Examiner* — Mark A Shabman
(74) *Attorney, Agent, or Firm* — W&K IP

(57) ABSTRACT

The present invention discloses an adjustable gas detection device for coal bed comprising a detection direction adjustment assembly, a suction head angle adjustment assembly and an analysis bin, wherein the suction head angle adjustment assembly includes a suction head first-level angle adjustment assembly and a suction head second-level angle adjustment assembly, and the suction head first-level angle adjustment assembly includes a suction head that sucks a gas through a suction pump and sends it into the analysis bin through a suction pipe for analysis; the detection direction adjustment assembly and the suction head angle adjustment assembly jointly adjust a position and a direction of the suction head. The gas detection device for coal bed of the present invention has many degrees of freedom, can quickly complete the angle adjustment, and realizes rapidly-oriented detection, as well as having advantages of high control efficiency, rapid response, flexibility and reliability.

9 Claims, 5 Drawing Sheets

ADJUSTABLE GAS DETECTION DEVICE FOR COAL BED

CROSS-REFERENCE TO RELATED APPLICATIONS

This application claims priority to Chinese Patent Application No. 201910264476.9 with a filing date of Apr. 2, 2019. The content of the aforementioned application, including any intervening amendments thereto, are incorporated herein by reference.

TECHNICAL FIELD

The present invention relates to a gas detection device for coal bed, in particular, to an adjustable gas detection device for coal bed.

BACKGROUND

Gas detector is an instrumentation tool for detecting leakage concentration of the gas, mainly refers to a handheld or fixed gas detector. It mainly uses a gas sensor to detect the type of gas present in the environment, and the gas sensor is a sensor for detecting the composition and content of the gas. At present, there are many shortcomings in the use of gas detection devices for coal bed, wherein the fixed detection device has disadvantages of low degree of freedom, inconvenient adjustment, small detection range, and hidden dangers of work safety.

For above problems, the present invention provides an adjustable gas detection device for coal bed, which is convenient in adjustment, and can improve the detection effect.

SUMMARY

In order to achieve above purpose, the present invention provides the following technical solution: an adjustable gas detection device for coal bed, comprising a detection direction adjustment assembly, a suction head angle adjustment assembly and an analysis bin, wherein the suction head angle adjustment assembly includes a suction head first-level angle adjustment assembly and a suction head second-level angle adjustment assembly, and the suction head first-level angle adjustment assembly includes a suction head, the suction head sucking a gas through a suction pump and sends it into the analysis bin through a suction pipe for analysis; the detection direction adjustment assembly and the suction head angle adjustment assembly jointly adjust a position and a direction of the suction head.

Further, preferably, the detection direction adjustment assembly includes a motor base and a mounting plate, the motor base is fixedly mounted with a direction adjustment motor, the direction adjustment motor passes through the motor base and is fixedly mounted with a No. 2 gear at its output end, and the No. 2 gear is engaged with a No. 1 gear, the No. 1 gear being fixedly connected to the analysis bin and driving the analysis bin to rotate.

Further, preferably, both ends of an upper end of the analysis bin respectively extend to a support rod and are fixedly connected to the support rod, an upper portion of the support rod is fixedly connected to the mounting plate, and the other end of the support rod is slidably connected to a mounting base through a No. 1 slider; the slider is in an inverted T shape, and the mounting base is correspondingly opened with a circular arc-shaped groove having a T-shaped cross section for limiting the slider; the mounting base is generally annular with a middle portion provided with a mounting rod for fixing the motor base.

Further, preferably, the suction head first-level angel adjustment assembly further includes an angle adjustment base, and the angle adjustment base is mainly composed of a lower mounting base, an upper mounting base and an adjustment ball, wherein both the lower mounting base and the upper mounting base are provided with clamping members, and a side of the clamping member adjacent to the adjustment ball has a curvature similar to that of the adjustment ball; both the upper mounting base and an upper end of the clamping member matched with the upper mounting base are opened with a circular hole for exposing the adjustment ball, and an upper end of the adjustment ball is provided with an angle output shaft extending upward in a radial direction thereof, the angle output shaft being fixedly connected to the suction pump.

Further, preferably, both sides of the upper mounting base and the lower mounting base are provided with a fixing base, and the fixing base is connected through an adjustment bolt.

Further, preferably, the suction head second-level angle adjustment assembly includes a straight rack, a chute, an angle adjustment motor and a strut; the straight rack is slidably disposed on the mounting plate, a side view of the straight rack is inverted T-shaped, and the mounting plate is correspondingly opened with a groove having a T-shaped cross section for limiting the straight rack; a middle portion of the mounting plate is opened with an yielding port, the straight rack is disposed at one side of the yielding port, and the angle adjustment motor is disposed at the other end of the yielding port.

Further, preferably, the straight rack is mounted with a sliding slot disposed perpendicular to the straight rack through the mounting hole, the chute is inserted into the yielding port, and a length of the yielding port is slightly larger than a length of the straight rack; the chute is slidably provided with a No. 2 slider, and a side of the No. 2 slider adjacent to the angle adjustment motor is fixed with a crank, and the other end of the crank is driven by an output end of the angle adjustment motor; the output end of the angle adjustment motor is a side adjacent to the straight rack, and the angle adjustment motor is fixed on the mounting plate through the motor base.

Further, preferably, the straight rack is engaged with a No. 3 gear, and the No. 3 gear is coaxially provided with a teeth-uncompleted gear; the teeth-uncompleted gear is engaged with a No. 4 gear, and a fixed rod is fixed on the No. 4 gear; the No. 3 gear, the teeth-uncompleted gear and the No. 4 gear are all rotatably disposed on a rear plate, and the rear plate is fixed on the mounting plate; the crank is rotated a turn to drive the No. 4 gear to rotate half a turn clockwise and half a turn counterclockwise.

Further, preferably, both a bottom center position of the analysis bin and a center position of the No. 1 gear are provided with a through hole for connecting the suction pipe, and the suction pipe is communicated with the analysis bin through the No. 1 gear; a top center position of the analysis bin is provided with a discharge port, and the discharge port may be connected to a ventilation device through a connecting pipe; the analysis bin is provided with a partition plate to divide the analysis bin into two cavities, one of which is communicated with the suction pipe and the other of which is provided with an analysis processing device and the discharge port, and the two cavities are communicated through the analysis processing device.

Further, preferably, the analysis processing device includes a gas sensor and a microprocessor, and the analysis processing device, the direction adjustment motor, and the angle adjustment motor are all controlled uniformly by a controller.

Compared with the prior art, the present invention has the following beneficial effects:

The invention may have two modes of operation: first, according to the specific working conditions, the orientation is required for detection, and at this time, the direction and angle of the suction head are adjusted by the running direction adjustment motor and the angle adjustment motor to realize the oriented detection; in addition, the direction adjustment motor and the angle adjustment motor may also be continuously opened, and the suction head continuously moves in three dimensions, including circular motion and swinging back and forth, thereby realizing range detection. The gas detection device for coal bed of the present invention has many degrees of freedom, may quickly complete the angle adjustment, and realizes rapidly-oriented detection, as well as having advantages of high control efficiency, rapid response, flexibility and reliability, so as to greatly reduce the safety hazard of the work safety.

Figure 1:
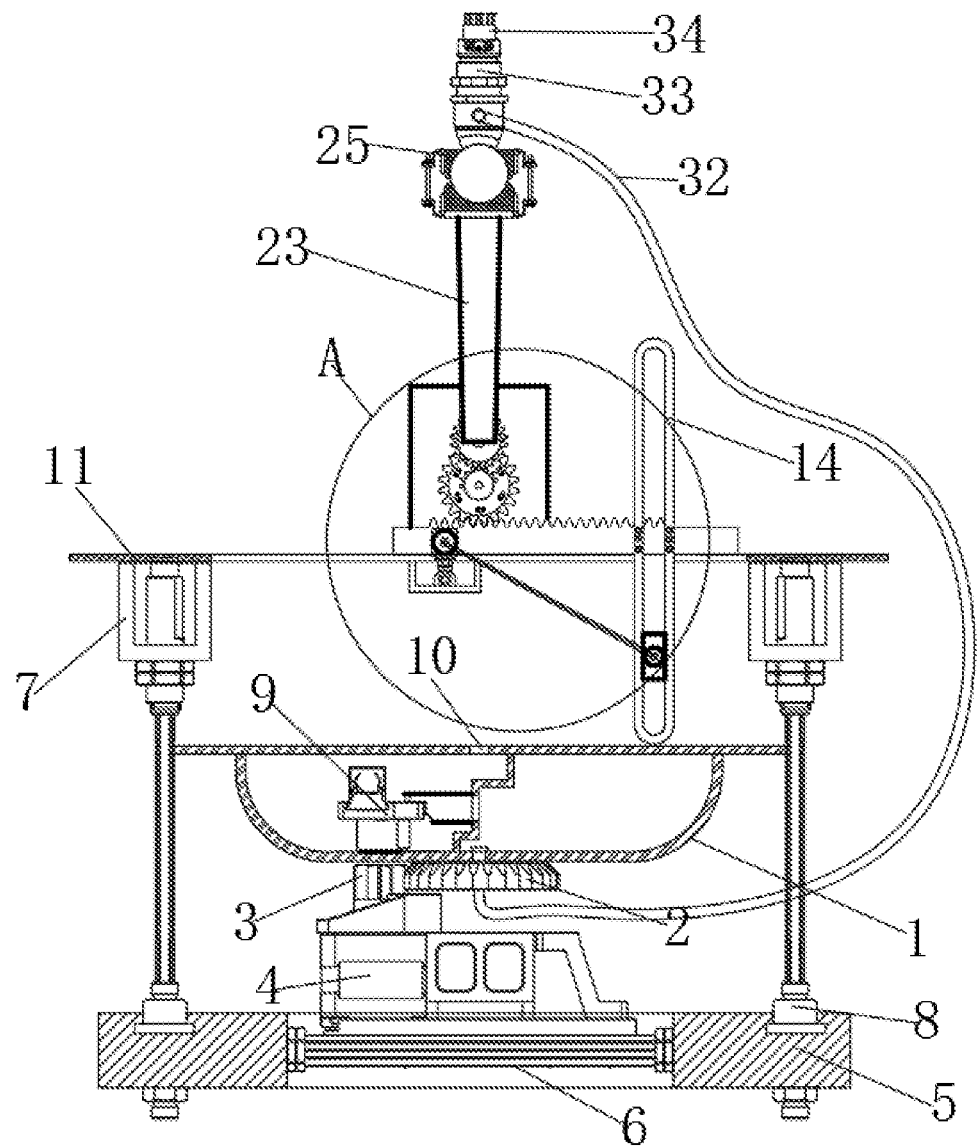
FIG. 1 is a view of the present invention.
Figure 2:
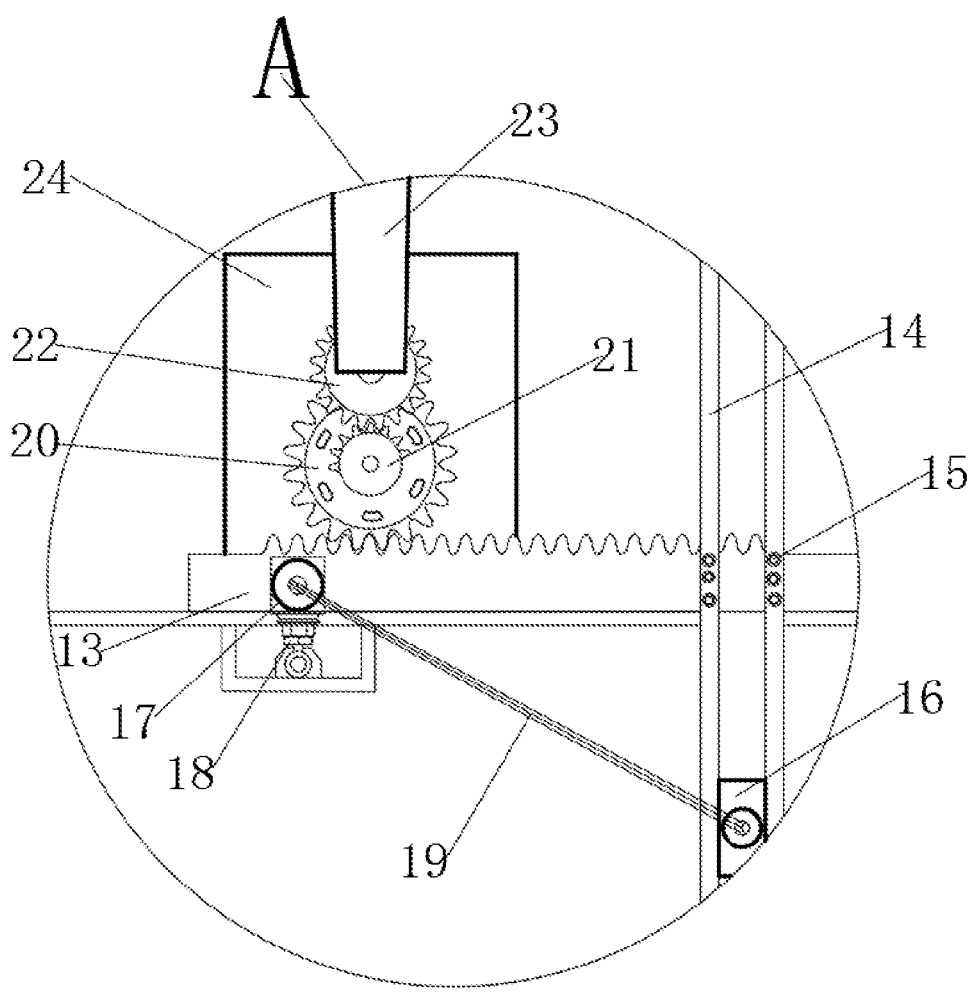
FIG. 2 is a partial enlarged view of A of the present invention.

1, analysis bin; 2, No. 1 gear; 3, No. 2 gear; 4, direction adjustment motor; 5, mounting base; 6, mounting rod; 7, support rod; 8, No. 1 slider; 9, analysis process device; 10, discharge port; 11, mounting plate; 12, yielding port; 13, straight rack; 14, chute; 15, mounting hole; 16, No. 2 slider; 17, angle adjustment motor; 18, motor base; 19, crank; 20, No. 3 gear; 21, teeth-uncompleted gear; 22, No. 4 gear; 25, angle adjustment base; 26, lower mounting base; 27, upper mounting base; 28, clamping block; 29, adjustment ball; 30, fixing base; 31, adjustment bolt; 32, suction pipe; 33, suction pump; 34, suction head.

DETAILED DESCRIPTION

The technical solutions in the embodiments of the present invention will be clearly and completely described hereafter in connection with the drawings in the embodiments of the present invention. It is apparent that the described embodiments are only a part of the embodiments of the present invention, but not the whole. On the basis of the embodiments in the present invention, all the other embodiments obtained by a person skilled in the art without involving an inventive effort are all concluded in the protection scope of the present invention.

With reference to FIGS. 1 to 5, the present invention provides a technical solution: an adjustable gas detection device for coal bed, characterized by comprising a detection direction adjustment assembly, a suction head angle adjustment assembly and an analysis bin 1, wherein the suction head angle adjustment assembly includes a suction head first-level angle adjustment assembly and a suction head second-level angle adjustment assembly, and the suction head first-level angle adjustment assembly includes a suction head 34, the suction head 34 sucking a gas through a suction pump 33 and sends it into the analysis bin 1 through a suction pipe 32 for analysis; the detection direction adjustment assembly and the suction head angle adjustment assembly jointly adjust a position and a direction of the suction head 34.

In the present embodiment, the detection direction adjustment assembly includes a motor base and a mounting plate 11, the motor base is fixedly mounted with a direction adjustment motor 4, the direction adjustment motor 4 passes through the motor base and is fixedly mounted with a No. 2 gear 3 at its output end, and the No. 2 gear 3 is engaged with a No. 1 gear 2, the No. 1 gear 2 being fixedly connected to the analysis bin 1 and driving the analysis bin 1 to rotate.

In the present embodiment, both ends of an upper end of the analysis bin 1 respectively extend to a support rod 7 and are fixedly connected to the support rod 7, an upper portion of the support rod 7 is fixedly connected to the mounting plate 11, so that the mounting plate 11 is driven to rotate when the direction adjustment motor 4 drives the analysis bin 1, and the other end of the support rod 7 is slidably connected to a mounting base 5 through a No. 1 slider 8; the slider 8 is in an inverted T shape, and the mounting base 5 is correspondingly opened with a circular arc-shaped groove having a T-shaped cross section for limiting the slider 8; the mounting base 5 is generally annular with a middle portion provided with a mounting rod 6 for fixing the motor base.

In the present embodiment, the suction head first-level angel adjustment assembly further includes an angle adjustment base 25, and the angle adjustment base 25 is mainly composed of a lower mounting base 26, an upper mounting base 27 and an adjustment ball 29, wherein both the lower mounting base 26 and the upper mounting base 27 are provided with clamping members 28, and a side of the clamping member 28 adjacent to the adjustment ball 29 has a curvature similar to that of the adjustment ball 29; both the upper mounting base 27 and an upper end of the clamping member 28 matched with the upper mounting base 27 are opened with a circular hole for exposing the adjustment ball 29, and an upper end of the adjustment ball 29 is provided with an angle output shaft extending upward in a radial direction thereof, the angle output shaft being fixedly connected to the suction pump 33; the first-level adjustment assembly performs an adjustment manually before operation, which is mainly used for initially adjusting the angle of the suction head, thereby facilitating disassembly and detection.

Among them, both sides of the upper mounting base 27 and the lower mounting base 26 are provided with a fixing base 30, and the fixing base 30 is connected through an adjustment bolt 31.

Figure 3:
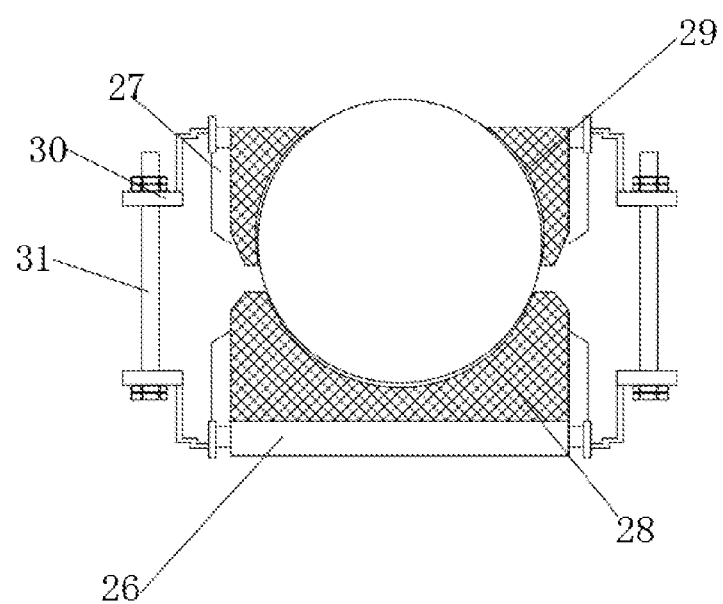
FIG. 3 is a view of an angle adjustment base of the present invention.
Figure 4:
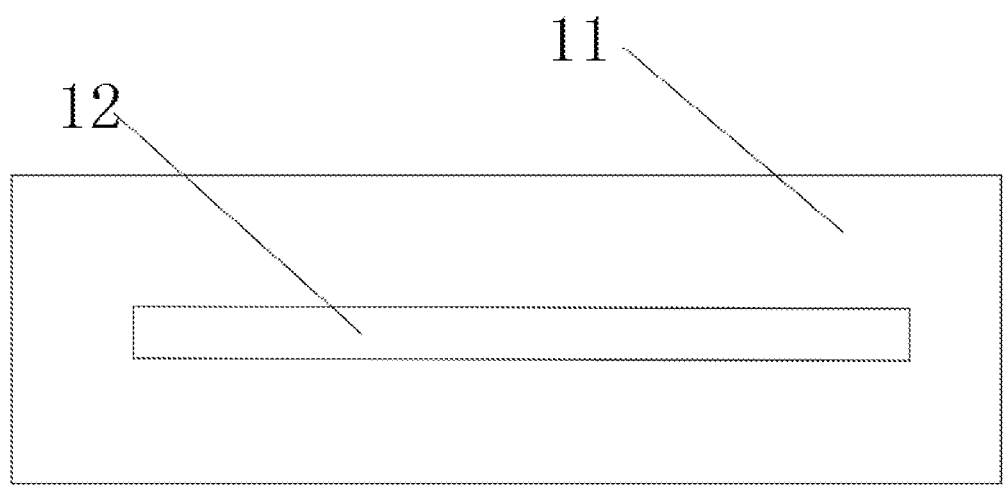
FIG. 4 is a top view of a mounting plate of the present invention.
Figure 5:
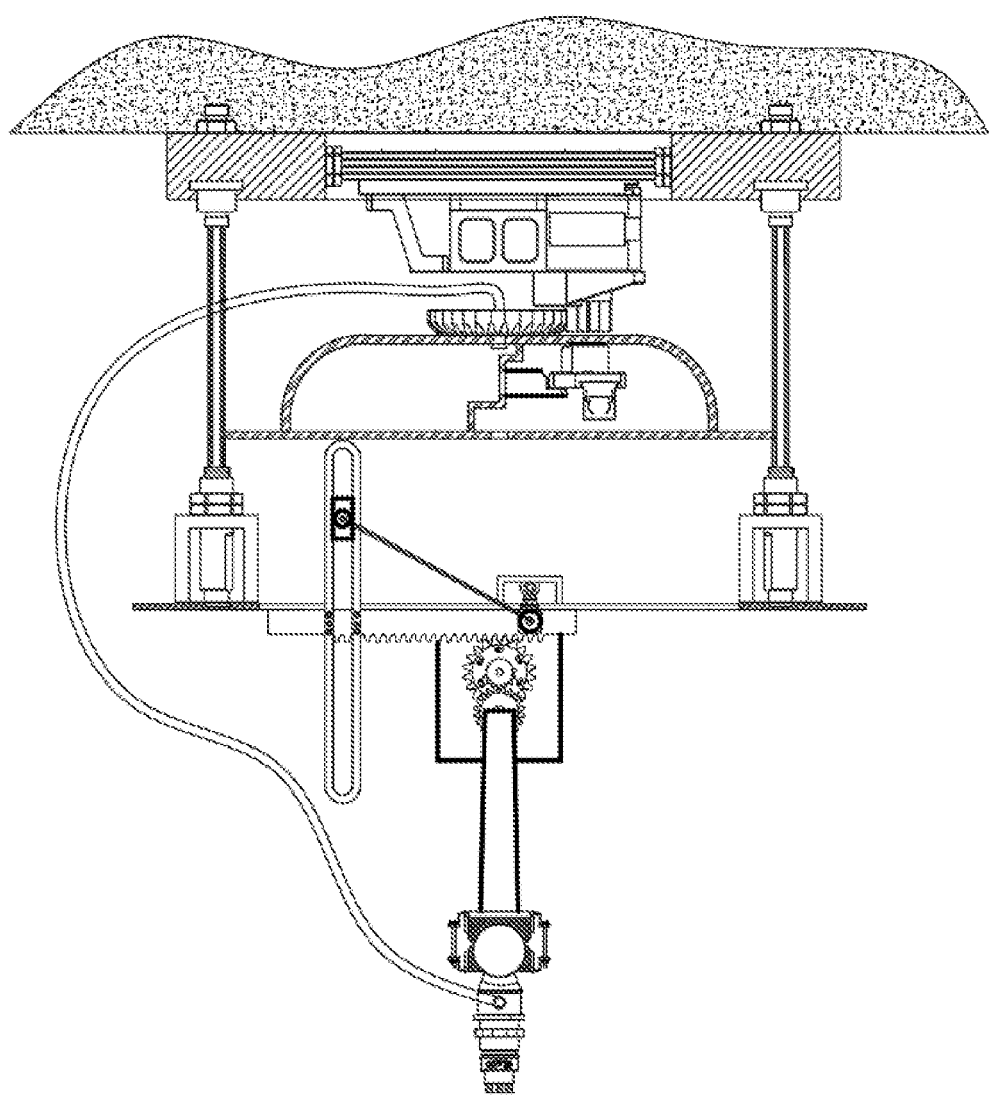
FIG. 5 is a view showing the assembly of the present invention.

In the present embodiment, the suction head second-level angle adjustment assembly includes a straight rack 13, a chute 14, an angle adjustment motor 17 and a strut 23; the straight rack 13 is slidably disposed on the mounting plate 11, a side view of the straight rack 13 is inverted T-shaped, and the mounting plate 11 is correspondingly opened with a groove having a T-shaped cross section (not shown) for limiting the straight rack 13; as shown in FIG. 3, a middle portion of the mounting plate 11 is opened with an yielding port 12, the straight rack 13 is disposed at one side of the yielding port 12, and the angle adjustment motor 17 is disposed at the other end of the yielding port 12.

In the present embodiment, the straight rack 13 is mounted with a sliding slot 14 disposed perpendicular to the straight rack 13 through the mounting hole 15, the chute 14 is inserted into the yielding port 12, and a length of the yielding port 12 is slightly larger than a length of the straight rack 13; the chute 14 is slidably provided with a No. 2 slider 16, and a side of the No. 2 slider 16 adjacent to the angle adjustment motor is fixed with a crank 19, and the other end of the crank 19 is driven by an output end of the angle adjustment motor 17; the output end of the angle adjustment motor 17 is a side adjacent to the straight rack 13, and the angle adjustment motor 17 is fixed on the mounting plate 90 through the motor base 18. In operation, the angle adjustment motor 17 drives the crank 19 to perform a circumferential operation, such as the position of the crank 19 shown in FIG. 1, and when rotating 90 degrees counterclockwise, the 90 degree rotation of the crank 19 counterclockwise may be decomposed into a rightward movement and an upward movement, wherein the rightward movement drives the straight rack to slide to the right, and the upward movement drives the No. 2 slider 26 to slide upward.

As a preferred embodiment, the straight rack 13 is engaged with a No. 3 gear 20, and the No. 3 gear 20 is coaxially provided with a teeth-uncompleted gear 21; the teeth-uncompleted gear 21 is engaged with a No. 4 gear 22, and a fixed rod 23 is fixed on the No. 4 gear 22; the No. 3 gear 20, the teeth-uncompleted gear 21 and the No. 4 gear 22 are all rotatably disposed on a rear plate 24, and the rear plate 24 is fixed on the mounting plate 11; when the crank 19 rotates by one turn, the straight rack 13 is driven to reciprocate once, and when the straight rack 13 reciprocates once, the No. 3 gear 20 may be driven to rotate clockwise by one turn and rotate counterclockwise by one turn, and when the teeth-uncompleted rear 21 rotates by one turn, the No. 4 gear 22 is driven to rotate by half a turn, so that the crank rotating by one turn may drive the No. 4 gear to rotate half a turn clockwise and half a turn counterclockwise; due to the many parameters of the gear, including the number of the teeth, the modulus, the diameter of the tip circle, the diameter of the root circle, etc., the calculation is complicated, so the specific number of teeth, the modulus, and the like are no longer provided.

In the present embodiment, both a bottom center position of the analysis bin 1 and a center position of the No. 1 gear 2 are provided with a through hole for connecting the suction pipe 32, and the suction pipe 32 is communicated with the analysis bin 1 through the No. 1 gear 2; a top center position of the analysis bin 1 is provided with a discharge port 10; the analysis bin 1 is provided with a partition plate to divide the analysis bin into two cavities, one of which is communicated with the suction pipe 32 and the other of which is provided with an analysis processing device 9 and the discharge port 10, and the two cavities are communicated through the analysis processing device 9; a gas entering the right cavity of the analysis bin 1 through the suction pipe 32 may be directly analyzed and processed by the analysis processing device 9, and then discharged through the discharge port 10, specifically through the ventilation pipe, to reduce the detection error.

Among them, the analysis processing device includes a gas sensor and a microprocessor, wherein the gas sensor and the micro-processing are used for detecting and analyzing the concentration component of the gas, etc., which are existing products and thus will not be described again; the analysis processing device 9, the direction adjustment motor 4, and the angle adjustment motor 17 are all controlled uniformly by a controller.

The invention may have two modes of operation: first, according to the specific working conditions, the orientation is required for detection, and at this time, the direction and angle of the suction head 34 are adjusted by running the direction adjustment motor 4 and the angle adjustment motor 17 to realize the oriented detection; in addition, only the direction adjustment motor 4 and the angle adjustment motor 17 may also be opened, and the suction head 34 continuously moves in three dimensions, including circular motion and swinging back and forth, thereby realizing range detection. The gas detection device for coal bed of the present invention has many degrees of freedom, may quickly complete the angle adjustment, and realizes rapidly-oriented detection, as well as having advantages of high control efficiency, rapid response, flexibility and reliability, so as to greatly reduce the safety hazard of the work safety.

Although the embodiments of the present invention have been shown and described, it can be understood that a person skilled in the art can make various changes, modifications, substitutions and variations to the embodiments without departing from the principle and spirit of the present invention; and the scope of the present invention is defined by the attached claims and equivalents thereof.

We claim:

1. An adjustable gas detection device for coal bed, comprising a detection direction adjustment assembly, a suction head angle adjustment assembly and an analysis bin (1), wherein the suction head angle adjustment assembly includes a suction head first-level angle adjustment assembly and a suction head second-level angle adjustment assembly, and the suction head first-level angle adjustment assembly includes a suction head (34), wherein the suction head (34) sucks a gas through a suction pump (33) and sends it into the analysis bin (1) through a suction pipe (32) for analysis; the detection direction adjustment assembly and the suction head angle adjustment assembly jointly adjust a position and a direction of the suction head (34);

wherein the detection direction adjustment assembly includes a motor base and a mounting plate (11), the motor base is fixedly mounted with a direction adjustment motor (4), wherein the direction adjustment motor (4) passes through the motor base and is fixedly mounted with a No. 2 gear (3) at its output end, and the No. 2 gear (3) is engaged with a No. 1 gear (2), the No. 1 gear (2) being fixedly connected to the analysis bin (1) and driving the analysis bin (1) to rotate.

2. The adjustable gas detection device for coal bed according to claim 1, wherein the analysis bin (1) comprises an upper end, the upper end comprises two sides, the two sides of the upper end of the analysis bin (1) respectively extend to a support rod (7) and are fixedly connected to the support rod (7), an upper portion of the support rod (7) is fixedly connected to the mounting plate (11), and the other end of the support rod (7) is slidably connected to a mounting base (5) through a No. 1 slider (8); the slider (8) is in an inverted T shape; the mounting base (5) is annular with a middle portion provided with a mounting rod (6) for fixing the motor base.

3. The adjustable gas detection device for coal bed according to claim 1, wherein the suction head first-level angle adjustment assembly further includes an angle adjustment base (25), and the angle adjustment base (25) is mainly composed of a lower mounting base (26), an upper mounting base (27) and an adjustment ball (29), wherein both the lower mounting base (26) and the upper mounting base (27) are provided with clamping members (28), and a side of the clamping member (28) adjacent to the adjustment ball (29) has a curvature similar to that of the adjustment ball (29); both the upper mounting base (27) and an upper end of the clamping member (28) matched with the upper mounting base (27) are opened with a circular hole for exposing the adjustment ball (29), and an upper end of the adjustment ball (29) is provided with an angle output shaft extending upward in a radial direction thereof, the angle output shaft being fixedly connected to the suction pump (33).

4. The adjustable gas detection device for coal bed according to claim 3, wherein the upper mounting base (27) comprises two sides, the two sides of the upper mounting base (27) and the lower mounting base (26) are provided with a fixing base (30), and the fixing base (30) slides through an adjustment bolt (31).

5. The adjustable gas detection device for coal bed according to claim 1, wherein the suction head second-level angle adjustment assembly includes a straight rack (13), a chute (14), an angle adjustment motor (17) and a strut (23); the straight rack (13) is slidably disposed on the mounting plate (11), a side view of the straight rack (13) is inverted T-shaped, and the mounting plate (11) is correspondingly opened with a groove having a T-shaped cross section; a middle portion of the mounting plate (11) is opened with a yielding port (12), the yield port (12) comprises two sides, the straight rack (13) is disposed at one side of the yielding port (12), and the angle adjustment motor (17) is disposed at the other end of the yielding port (12).

6. The adjustable gas detection device for coal bed according to claim 5, wherein the straight rack (13) is mounted with a sliding slot (14) disposed perpendicular to the straight rack (13) through the mounting hole (15), the chute (14) is inserted into the yielding port (12), and a length of the yielding port (12) is larger than a length of the straight rack (13); the chute (14) is slidably provided with a No. 2 slider (16), the No. 2 slider (16) comprises two sides, and a side of the No. 2 slider (16) adjacent to the angle adjustment motor is fixed with a crank (19), the angle adjustment motor (17) comprises an output end, and the other end of the crank (19) is driven by the output end of the angle adjustment motor (17); the output end of the angle adjustment motor (17) is a side adjacent to the straight rack (13), and the angle adjustment motor (17) is fixed on the mounting plate (11) through the motor base (18).

7. The adjustable gas detection device for coal bed according to claim 6, wherein the straight rack (13) is engaged with a No. 3 gear (20), and the No. 3 gear (20) is coaxially provided with a teeth-uncompleted gear (21); the teeth-uncompleted gear (21) is engaged with a No. 4 gear (22), and a fixed rod (23) is fixed on the No. 4 gear (22); the No. 3 gear (20), the teeth-uncompleted gear (21) and the No. 4 gear (22) are all rotatably disposed on a rear plate (24), and the rear plate (24) is fixed on the mounting plate (11).

8. The adjustable gas detection device for coal bed according to claim 1, wherein both a bottom center position of the analysis bin (1) and a center position of the No. 1 gear (2) are provided with a through hole for connecting the suction pipe (32), and the suction pipe (32) is communicated with the analysis bin (1) through the No. 1 gear (2); a top center position of the analysis bin (1) is provided with a discharge port (10), and the discharge port (10) is connected to a ventilation device through a connecting pipe; the analysis bin (1) is provided with a partition plate to divide the analysis bin into two cavities, one of which is communicated with the suction pipe (32) and the other of which is provided with an analysis processing device (9) and the discharge port (10), and the two cavities are communicated through the analysis processing device (9).

9. The adjustable gas detection device for coal bed according to claim 8, comprising an analysis processing device (9), wherein the analysis processing device (9) includes a gas sensor and a microprocessor, and the analysis processing device (9), the direction adjustment motor (4), and the angle adjustment motor (17) are all controlled uniformly by a controller.

\* \* \* \* \*